(12) United States Patent
Storck et al.

(10) Patent No.: US 12,115,581 B2
(45) Date of Patent: Oct. 15, 2024

(54) RAPID MATERIAL DEVELOPMENT PROCESS FOR ADDITIVE MANUFACTURED MATERIALS

(71) Applicant: The Johns Hopkins University, Baltimore,, MD (US)

(72) Inventors: Steven M. Storck, Catonsville, MD (US); Joseph J. Sopcisak, Derwood, MD (US); Christopher M. Peitsch, Perry Hall, MD (US); Salahudin M. Nimer, Fulton, MD (US); Zachary R Ulbig, Essex, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 18/472,906

(22) Filed: Sep. 22, 2023

(65) Prior Publication Data
US 2024/0017326 A1 Jan. 18, 2024

Related U.S. Application Data

(62) Division of application No. 17/320,443, filed on May 14, 2021, now Pat. No. 11,806,784.
(Continued)

(51) Int. Cl.
*B22F 10/85* (2021.01)
*B22F 10/28* (2021.01)
(Continued)

(52) U.S. Cl.
CPC .............. *B22F 10/85* (2021.01); *B22F 10/28* (2021.01); *B22F 12/90* (2021.01); *B33Y 10/00* (2014.12); *B33Y 30/00* (2014.12); *B33Y 50/02* (2014.12)

(58) Field of Classification Search
CPC .......... B22F 10/85; B22F 10/28; B22F 12/90; B22F 2999/00; B22F 10/36;
(Continued)

(56) References Cited

U.S. PATENT DOCUMENTS 11,806,784 B2 * 11/2023 Storck ................... B33Y 50/02
2020/0038953 A1 * 2/2020 Pavan ..................... B22F 10/10
2022/0011745 A1 * 1/2022 Bae ......................... B33Y 50/00

* cited by examiner

*Primary Examiner* — Michael J Brown
(74) *Attorney, Agent, or Firm* — Sung T. Kim

(57) ABSTRACT

A rapid material development process for a powder bed fusion additive manufacturing (PBF AM) process generally utilizes a computational fluid dynamics (CFD) simulation to facilitate selection of a simulated parameter set, which can then be used in a design of experiments (DOE) to generate an orthogonal parameter space to predict an ideal parameter set. The orthogonal parameter space defined by the DOE can then be used to generate a multitude of reduced volume build samples using PBF AM with varying laser or electron beam parameters and/or feedstock chemistries. The reduced volume build samples are mechanically characterized using high throughput techniques and analyzed to provide an optimal parameter set for a 3D article or a validation sample, which provides an increased understanding of the parameters and their independent and confounding effects on defects and microstructure. Additionally, machine learning techniques can be used to optimize for future parameter selection by modeling the relationship between input processing parameters and outputs of material characterization.

20 Claims, 15 Drawing Sheets

Related U.S. Application Data

(60) Provisional application No. 63/028,131, filed on May 21, 2020.

(51) Int. Cl.
  *B22F 12/90* (2021.01)
  *B33Y 10/00* (2015.01)
  *B33Y 30/00* (2015.01)
  *B33Y 50/02* (2015.01)
  *B22F 10/20* (2021.01)
  *B22F 10/36* (2021.01)

(58) Field of Classification Search
  CPC ...... B22F 2203/03; B22F 10/20; B33Y 10/00; B33Y 30/00; B33Y 50/02; G16C 60/00; Y02P 10/25
  USPC .......................................................... 419/1
  See application file for complete search history.

RAPID MATERIAL DEVELOPMENT PROCESS FOR ADDITIVE MANUFACTURED MATERIALS

CROSS-REFERENCE TO RELATED APPLICATIONS

This application is a divisional patent application of U.S. patent application Ser. No. 17/320,443, filed on May 14, 2021, which claims the benefit of U.S. Provisional Application Ser. No. 63/028,131, filed on May 21, 2020, which are incorporated by reference herein in their entirety.

BACKGROUND

The present disclosure generally relates to rapid material development processes for additive manufactured materials. More particularly, the rapid material development processes utilize simulation and intelligent design following the simulation to build and analyze multiple reduced volume samples from different feedstock chemistries and/or different laser parameters. Physical outputs of the multiple reduced volume samples are quantified by mechanical characterization to allow for rapid optimization and adjustment of the process control parameters so as to select a desired quality and provide a robust processing space. In this manner, one can predict material formation with respect to defects or microstructure and the relevant mechanical performance associated with the material synthesis.

Additive manufacturing (AM) processes are fabrication techniques that allow one to produce functional complex parts layer-by-layer, without the use of molds or dies. AM processes allow for fabrication of complex design features to be incorporated. There are a variety of methods of additive manufacturing utilizing a variety of different feedstock materials, e.g., plastics, metals, ceramics, composites, or the like. For example, powder bed fusion (PBF) is a subset of additive manufacturing (AM), wherein a thermal energy source such as that generated by a laser (L-PBF) or an electron beam (E-PBF) or directed energy deposition (DED) is used to consolidate material in powder form to form three-dimensional (3D) articles. The thermal energy source is applied to particles contained within a powder bed to melt, sinter or fuse the particles together. The powder bed is subsequently indexed down as each layer is completed to allow new powder to be spread over the build area, and for the layer-by-layer consolidation process to be continued.

A typical PBF AM process begins with creation of a digital model that is converted into a computer file, or computer aided design ("CAD") data, defining the three dimensional article in two-dimensional layers, which typically range in thickness from about 20 micrometers to about 100 micrometers. The CAD data can include geometric data relating to a size, shape, thickness, material, mass, or density of the article, as well as internal features, passages, and structures. Next, a layer of powder material is deposited on a work platform. A heat source, such as a laser or an electron beam, then selectively melts, sinters, or fuses the metallic powder over the platform. Once cooled, the melted, sintered or fused pattern becomes the first layer that is used to define the article. After the first layer is formed, the platform, along with the two-dimensional pattern in the first layer, lowers and un-fused powder fills in the void over the first layer. That powder is then melted, sintered, or fused to form a second layer. The process of building the article a single layer at a time is repeated until the complete 3D article is manufactured. Powder bed fusion methods work well with metals as well as plastics, polymers, composites and ceramics.

As noted above, PBF AM is a heat driven process, which needs to be modeled accurately. The large temperature gradients exhibited by PBF AM processes, for example, justify using temperature-dependent properties such as absorbance, thermal diffusivity, surface tension and vapor pressure, which can strongly impact the final solidified structure during modeling.

BRIEF SUMMARY

Disclosed herein are systems, computer implemented powder bed fusion rapid material development processes for additive manufactured materials, and non-transitory computer readable mediums that when executed by a processor, causes the processor to execute operations for parameter optimization of a powder fusion bed additive manufacturing process.

In one or more embodiments, the systems include at least one computer communicatively coupled to a three-dimensional additive manufacturing printer; and a mechanical characterization device configured to measure one or more physical outputs associated with additive manufactured reduced volume samples. The additive manufactured reduced volume samples are a fraction of an intended build article, and the at least one computer is configured to provide a computational fluid dynamic simulation of a powder bed fusion additive manufacturing process and provide a simulated optimal parameter set. The at least one computer is further configured to provide a first statistical design of experiments based on the simulated optimal parameter set to generate a multi-factorial parameter space encompassing the simulated optical parameter set and provide instructions to the three-dimensional additive manufacturing printer to build the reduced volume samples according to the multi-factorial parameter space to determine a first optimal build parameter set. The at least one computer is optionally configured to provide at least one additional statistical design of experiments based on the first optimal build parameter set to generate at least one additional multi-factorial parameter space encompassing the first optimal build parameter set and provide instructions to the three-dimensional additive manufacturing printer to build the reduced volume samples according to the at least one additional multi-factorial parameter space to determine at least one additional optimal build parameter set from the first optimal build parameter set.

In one or more embodiments, a computer implemented powder bed fusion rapid material development process for additive manufactured materials, the computer implemented process includes modeling melt pool solidification of the powder bed fusion additive manufactured materials to produce a simulated parameter set; designing a multi-factorial parameter space encompassing the simulated parameter set; building multiple additive manufactured samples for each parameter set within the multi-factorial parameter space, wherein the parameter set comprises independent parameters comprising layer thickness, hatch spacing, exposure time, scan velocity, power or combinations thereof, and wherein the samples are at a reduced volume relative to an intended build article; mechanically characterizing one or more physical outputs for each of the samples built according to each parameter set; and correlating defect morphology associated with the one or more of physical outputs to one or more independent parameters within the multi-factorial parameter space used in building the multiple additive manufactured samples to provide an optimal parameter set.

In one or more embodiments, a non-transitory computer readable medium embodying computer-executable instructions, that when executed by a processor, causes the processor to execute operations for parameter optimization of a powder fusion bed additive manufacturing process includes modeling melt pool solidification for a feedstock composition to produce a simulated parameter set; executing a multi-factorial design of experiments to define a parameter space encompassing the simulated parameter set; providing instructions to a three dimensional additive manufacturing printer to build multiple samples associated with each parameter set within the parameter space, wherein each parameter set comprises one or more of a layer thickness, a hatch spacing, an exposure time, a scan velocity, a power or combinations thereof, and wherein the samples are at a reduced volume relative to an intended build article; mechanically characterizing one or more physical outputs for each of the multiple additive manufactured samples; and correlating defect morphology associated with the one or more physical outputs to one or more of the parameters used in building the multiple additive manufactured samples to provide an optimized parameter set.

The disclosure may be understood more readily by reference to the following detailed description of the various features of the disclosure and the examples included therein.

BRIEF DESCRIPTION OF THE DRAWINGS

Referring now to the figures wherein the like elements are numbered alike.

DETAILED DESCRIPTION

Figure 1A:
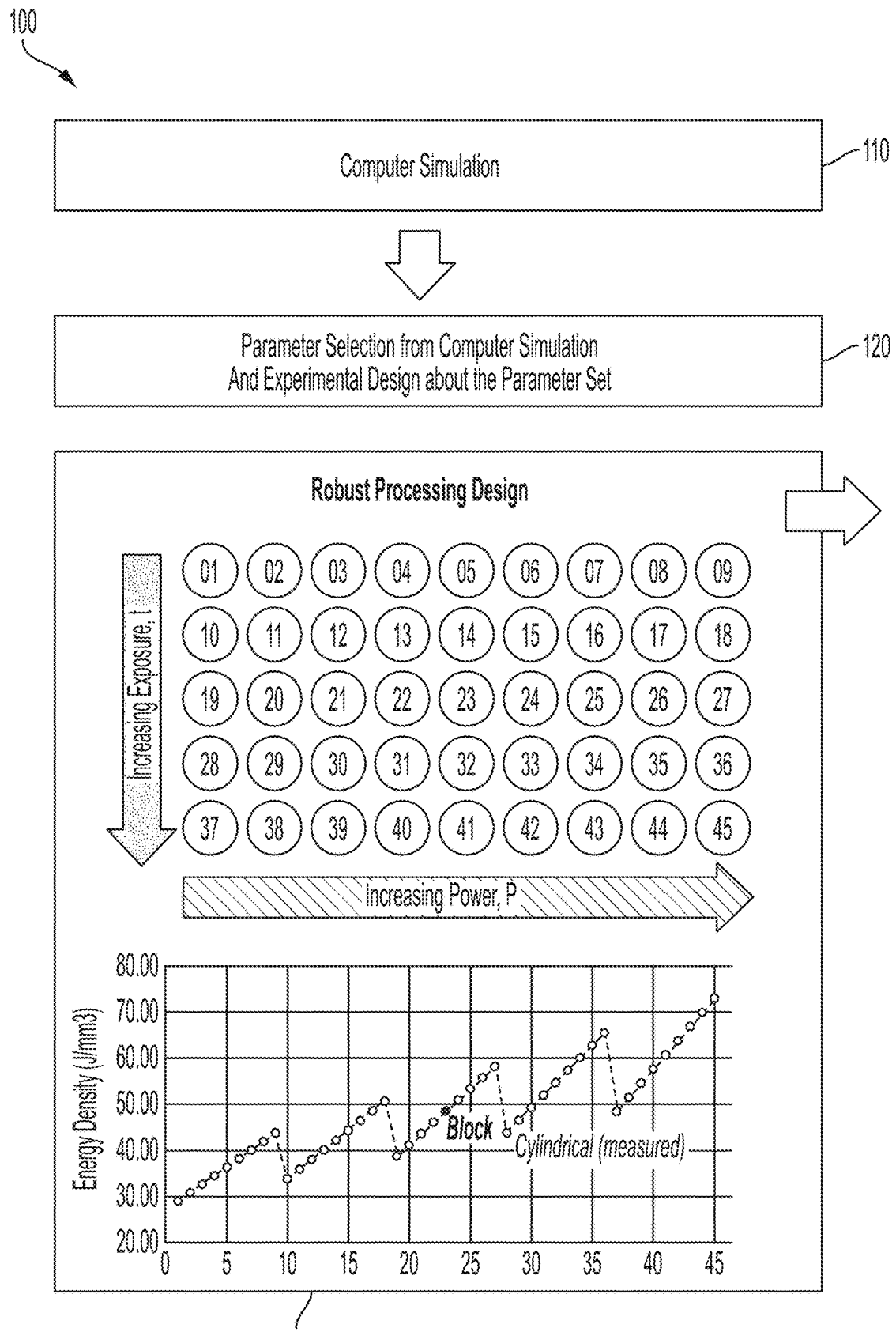
FIG. 1A-C depicts an exemplary process flow for rapidly down selecting AM machine parameters to improve processing space in accordance with the present disclosure.

Disclosed herein are processes for rapidly developing materials for powder bed fusion (PBF) additive manufacturing (AM). PBF AM utilizes a heat source to melt, sinter and/or fuse particles within a powder bed, wherein typically the heat source is a laser (L-PBF) or an electron beam (E-PBF). The rapid development processes for PBF AM described herein generally utilize a computer simulation model such as computational fluid dynamics (CFD) simulation to facilitate selection of a simulated parameter set, which can then be used in a design of experiments (DOE) to generate an orthogonal parameter space about the simulated parameter set to predict an optimized parameter set based on sample analysis. Additionally, machine learning techniques can be used to optimize for future parameter selection by modeling the relationship between input processing parameters and outputs of material characterization. Such models can make predictions for points not covered by the initial DOE. The CFD simulation can be used to effectively relate model output direct defect formation and microstructural distributions.

The orthogonal parameter space defined by the DOE is used to generate a multitude of reduced volume build samples using PBF AM with varying laser or electron beam parameters and/or feedstock chemistries. The reduced volume samples are a fraction of an intended build article and are configured to be amenable for analysis using a variety of mechanical characterization techniques. Accordingly, the physical outputs of these reduced volume build samples are mechanically characterized and analyzed to provide the optimal parameter set for a 3D article or a validation sample, which can provide an increased understanding of the parameters and their independent and confounding effects on defects and microstructure. Unlike a design that changes one factor at a time, which is relatively inefficient, the DOE can be used to determine the relative sensitivities of the different parameters, e.g., hatch spacing, laser power, velocity, layer thickness, recoating time, recoater speed, gas flow rate, gas concentration and/or the like, to provide an optimal parameter space. Prior PBF AM processes generally relied on manufacturer recommendations for selection of processing parameters, which may or may not exist and are not always optimal; relied on visual inspection, which is subjective and has relatively low sensitivity; and/or relied on laboratory scale characterization, which is typically time-consuming and expensive as well as requiring complex data reduction.

Conventional techniques related to additive manufacturing processes for forming three-dimensional articles may or may not be described in detail herein. Moreover, the various tasks and process steps described herein can be incorporated into a more comprehensive procedure or process having additional steps or functionality not described in detail herein. In particular, various steps in the additive manufacture of three-dimensional articles are well known and so, in the interest of brevity, many conventional steps will only be mentioned briefly herein or will be omitted entirely without providing the well-known process details.

For the purposes of the description hereinafter, the terms "upper", "lower", "top", "bottom", "left," and "right," and derivatives thereof shall relate to the described structures, as they are oriented in the drawing figures. The same numbers in the various figures can refer to the same structural component or part thereof. Additionally, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

Spatially relative terms, e.g., "beneath," "below," "lower," "above," "upper," and the like, can be used herein for ease of description to describe one element or feature's relationship to another element(s) or feature(s) as illustrated in the figures.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the term "about" modifying the quantity of an ingredient, component, or reactant of the invention employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like.

It will also be understood that when an element, such as a layer, region, or substrate is referred to as being "on" or "over" another element, it can be directly on the other element or intervening elements can also be present. In contrast, when an element is referred to as being "directly on" or "directly over" another element, there are no intervening elements present, and the element is in contact with another element.

Figure 1B:
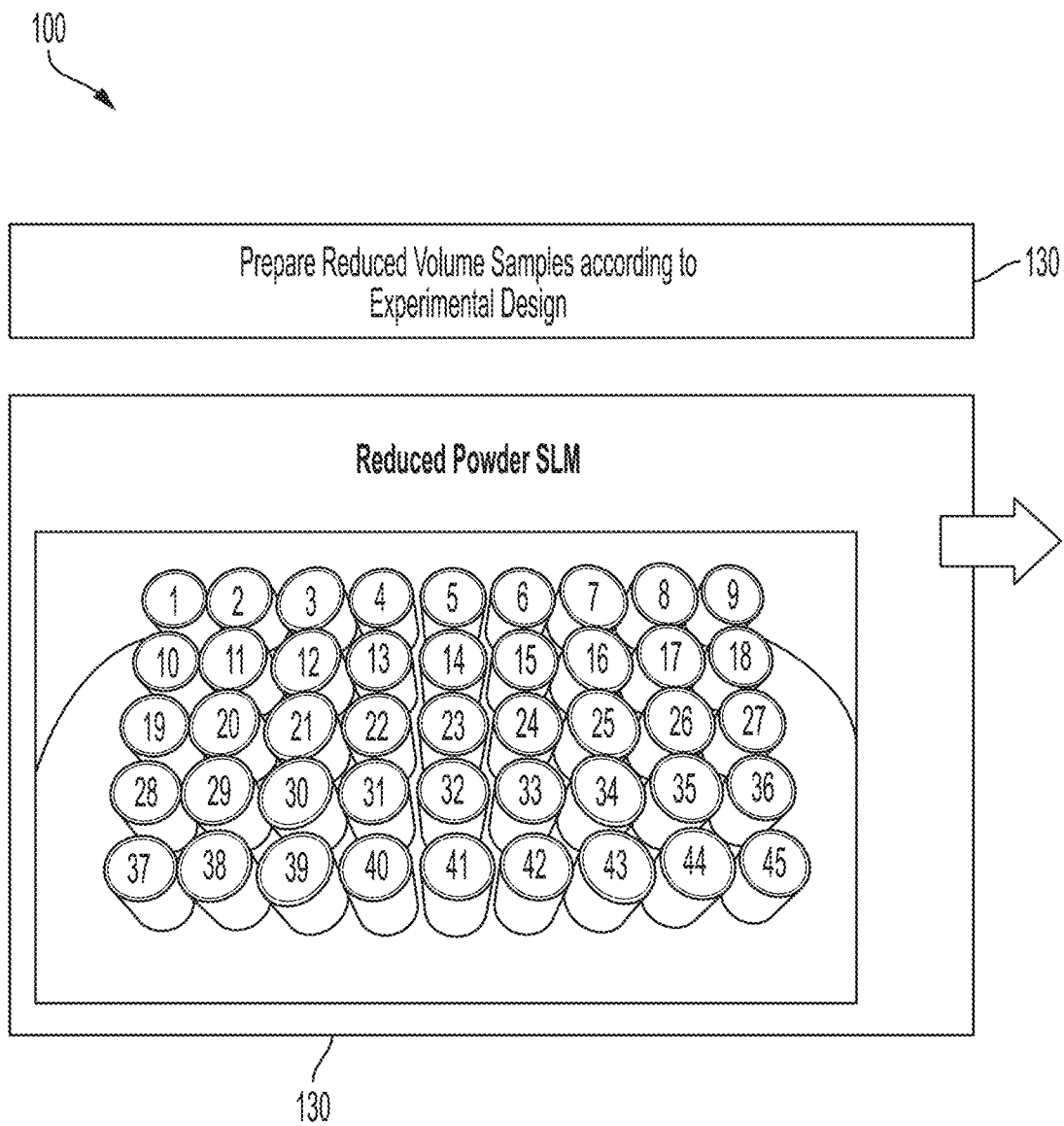
Figure 1C:
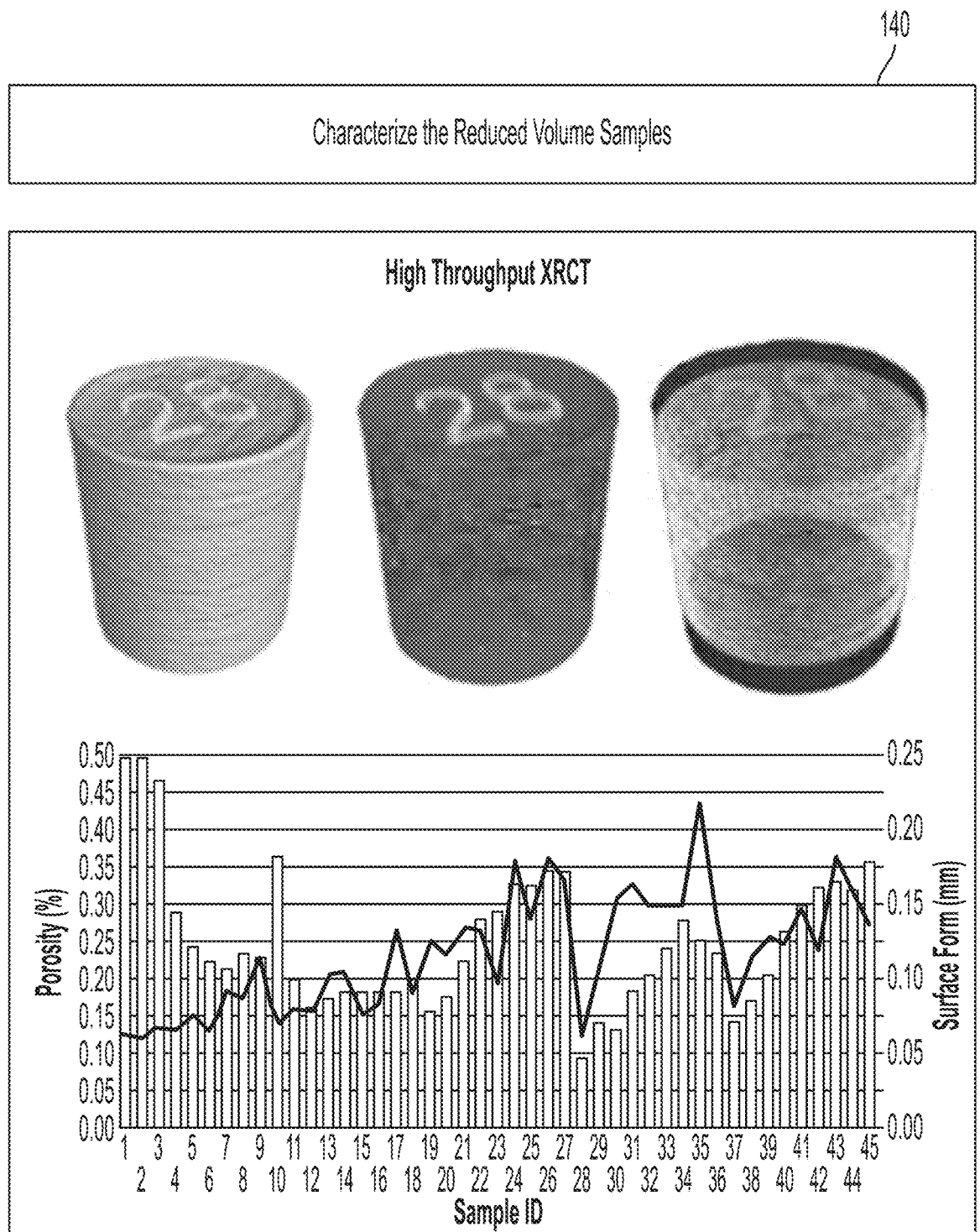

Referring now to FIG. 1A-C, there is shown an exemplary rapid development process flow for PBF AM in accordance with the present disclosure, generally designated by reference numeral 100, to provide an optimal parameter space for a particular 3D article build.

In block 110 as shown in FIG. 1A, a computer simulation process such as CFD simulation of the PBF AM process is utilized to rapidly scan the parameter space, e.g., determine an ideal energy density, and establish a baseline parameter space that predicts a desired melt pool shape and solidification. The CFD simulation can provide different simulated melt pool shapes including porosity formation within the melt pool based on simulated energy densities during the PBF AM process. An exemplary CFD modeling software for optimizing process parameters is FLOW-3D AM, which is commercially available from FLOW-3D.

As noted above, CFD simulation can be used to stimulate and analyze PBF AM process to provide simulations of melt pool dynamics and porosity formation for subsequent analysis and optimization of the process parameters. For example, macroscopic porosity (with pore sizes greater than the CFD modeling mesh size) can be extracted and characterized against mechanical characterization data such as, for example, X-ray computed tomography (XRCT) from an actual line track or three-dimensional specimen. Metrics such as size and shape can be quantified and locally compared along a single track, including the start and end of track, where defects often occur despite having optimal laser parameters. In addition, porosity smaller than the CFD modeling mesh size can be estimated using this technique by tracking evaporated gas particles. These data can be compared with a suitable mechanical characterization technique on the reduced volume build samples for validation. Once validated, the data can be used to generate a robust processing space.

The melt pool simulations can be performed using CFD layer by layer. For example, melt pool simulations can be made on the first melt layer of a selective laser melting (SLM) process and additional layers by specifying the laser process parameters. This process can be repeated several times to evaluate the fusing between consecutively solidified layers and the temperature gradients within the build while also monitoring the formation of porosity or other defects. This information is then used to predict the material density (or presence of porosity defects) and microstructure.

The CFD simulation can occur on an AM printer used for PBF, on a user's directly connected personal computer ("PC"), on a local computer connected by a local area network or using cloud computing. The parameters generated from the CFD simulation can include, but are not limited to, ambient conditions such as temperature, humidity and pressure; build speed; material conditions such as temperature and viscosity; layer thickness; and power profiles of the energy beam.

In block 120, also shown in FIG. 1A, a parameter set is selected from the CFD simulation and used to develop a robust and intelligent design of experiments (DOE) that utilizes a relatively large sample set. The statistics-based DOE allows multifactorial sampling of an orthogonal parameter space and elucidates the sensitivity of each parameter being examined, e.g., hatch spacing, laser power, velocity, layer thickness, and the like. In fact, an intelligent design paired with a large sample set allows for separation of processing parameters in order to find relationships and trends. In this manner, variability in process and between hardware can be readily and easily compared.

In block 130 as shown in FIG. 1B, samples are made in a PBF AM device in accordance with the DOE to statistically sample the independent processing parameters about the simulated parameter set. The sample set can be made with a reduced build volume to minimize cost, powder volume, and build time. Advantageously, the sample set can expeditiously be built on the same substrate and subsequently removed from the substrate for mechanical characterization. In one or more embodiments, the PBF AM process can be configured to provide each sample with different identification for ease in subsequent analysis. For example, the different samples can be consecutively numbered as shown in block 130. The reduced build volume is a fraction of the build volume for the intended 3D article to be built. Moreover, the reduced build volume can take any form amenable to subsequent high throughput mechanical characterization.

In block 140, as shown in FIG. 1C, the reduced volume build samples are characterized using high throughput characterization techniques such as X-ray computed tomography (XRCT) to down select the most desired processing parameters. The particular mechanical characterization technique is not intended to be limited. Exemplary mechanical characterization techniques include, without limitation, optical and X-ray microscopy, Archimedes method, microhardness, tensile strength, and the like. The various mechanical characterization techniques can be used, for example, to characterize porosity such as by measuring surface roughness, tensile strength, hardness, dimensional accuracy, percent volume fraction, size and shape deviation, type of defect, e.g., lack of fusion or keyhole, defect distribution, i.e., edge defects compared to infill defects, and the like. For example, the Archimedes method is a classic approach for determining the density of a sample, using $\rho = (Ma/Ma-Mw) \rho W$ (1) where $\rho W$ is the density of water, Ma is the mass of the sample as measured in air, and Mw is the mass of the sample as measured in water. Once the density is measured, if the bulk density is also known, then the sample's porosity can be calculated.

The mechanical characterization of the sample set generated from the DOE can be used to predict the ideal parameter set to be used for the 3D article to be built. For example, total porosity can be determined for a given parameter space defined by the DOE as a function of increasing energy density and increasing exposure times, which can be mechanically analyzed to determine an optimal parameter space for building the 3D article, which can have a significantly larger volume and a completely different geometry. For example, mechanical characterization of a sample set using high throughput XRCT can take the form of relatively small diameter cylinders conducive to substantially complete volume analysis by XRCT whereas for tensile strength mechanical characterization the sample set can take the form of non-standard reduced sized elongated bars as generally defined in ASTM E8. The particular shape and form of the reduced volume sample set are not intended to be limited and are generally dimensioned to provide confident analysis by the mechanical characterization technique.

With regard to XRCT, the reduced volume sized samples permit the use of this particular mechanical characterization technique for high throughput material development. XRCT is a technique that obtains X-ray images through a sample as it is rotated. The specimen is subjected to X-rays from many angles by rotating the specimen through approximately 1,000 small angular increments between 0 and 360°. In one or more embodiments conducive to high throughput processing, the cylinder diameter is less than about 10 millimeters. In one or more embodiments, the cylinder diameter is less than about 7 millimeters and in still one or more other embodiments, the cylinder diameter is less than about 5 millimeters.

XRCT had previously only been used for qualification of a 3D article and/or for failure analysis. However, because the reduced volume samples are a fraction of the volume used for the intended 3D article build and the geometries can be selected to be amenable for use in high throughput XRCT, XRCT can now be used for porosity characterization in material development to rapidly identify defect characteristics, which can be correlated back to the feedstock chemistry and/or input energy. Voxel resolution on the order of about 10 to about 20 micrometers can be obtained with cycle times of about 1 to 2 minutes. Block 140 pictorially illustrates sample 28 of an exemplary DOE showing the raw processed CT for the cylinder volume (left), a processed defect analysis showing the defects (center), and processed and computed internal meshed volume (right). As shown, the raw data was processed down to the defect segmentation. Once the image is segmented, the defects can be exported into a near surface and volume using the meshed sample. Total porosity for each of the different samples in the sample set is also graphically shown for the exemplary DOE.

Figure 2:
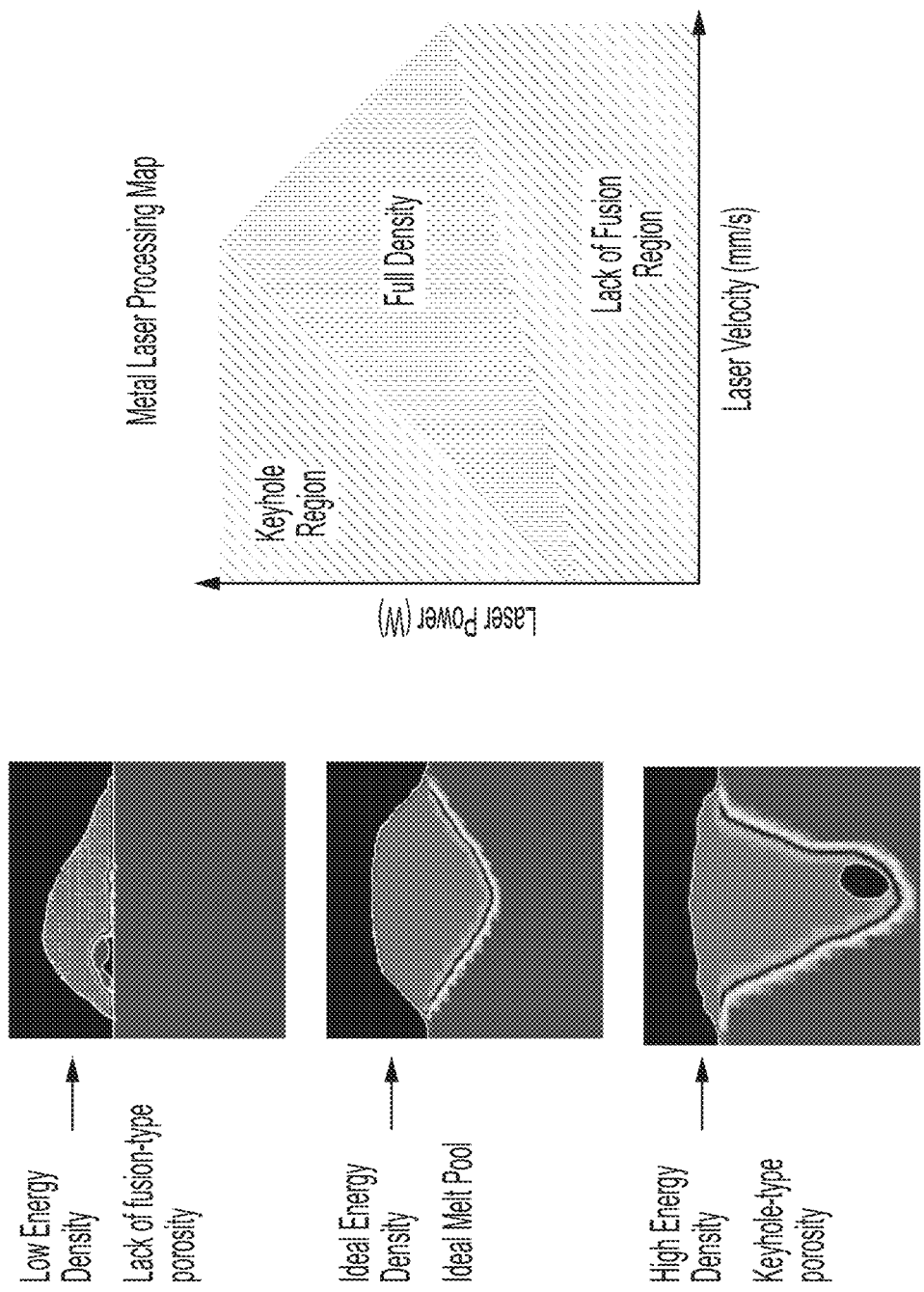
FIG. 2 pictorially and graphically illustrates simulation of an exemplary melt pool solidification depicting the formation of a lack of fusion defect (top left), an ideal melt pool solidification having full density (center left), a keyhole defect (bottom left), and a resulting laser power-velocity processing space (right) generated from the simulation data in accordance with the present disclosure.

FIG. 2 pictorially and graphically depicts an exemplary CFD simulation of an melt pool solidification in a laser powder bed fusion (L-PBF) AM process depicting the formation of a lack of fusion defect generally resulting from a low energy density during AM processing (top left), an ideal melt pool solidification having full density (center left), and a keyhole defect resulting from a high energy density during AM processing (bottom left), and the resulting laser power-velocity processing space (right) graphically generated from the simulation data. The parameter effects on energy density can be readily characterized and used to understand the laser-material intersections, and also can be used to take into account layer thickness, which can also affect the laser interaction volume. As layer thickness increases, the volume of material melted is increased non-linearly, which can shift "defect-free" processing regions, in unexpected directions. The present disclosure can be used to provide a processing space that avoids these shifts leading to an optimal "ideal melt pool" processing space that can be utilized to form a desired 3D article.

Figure 3:
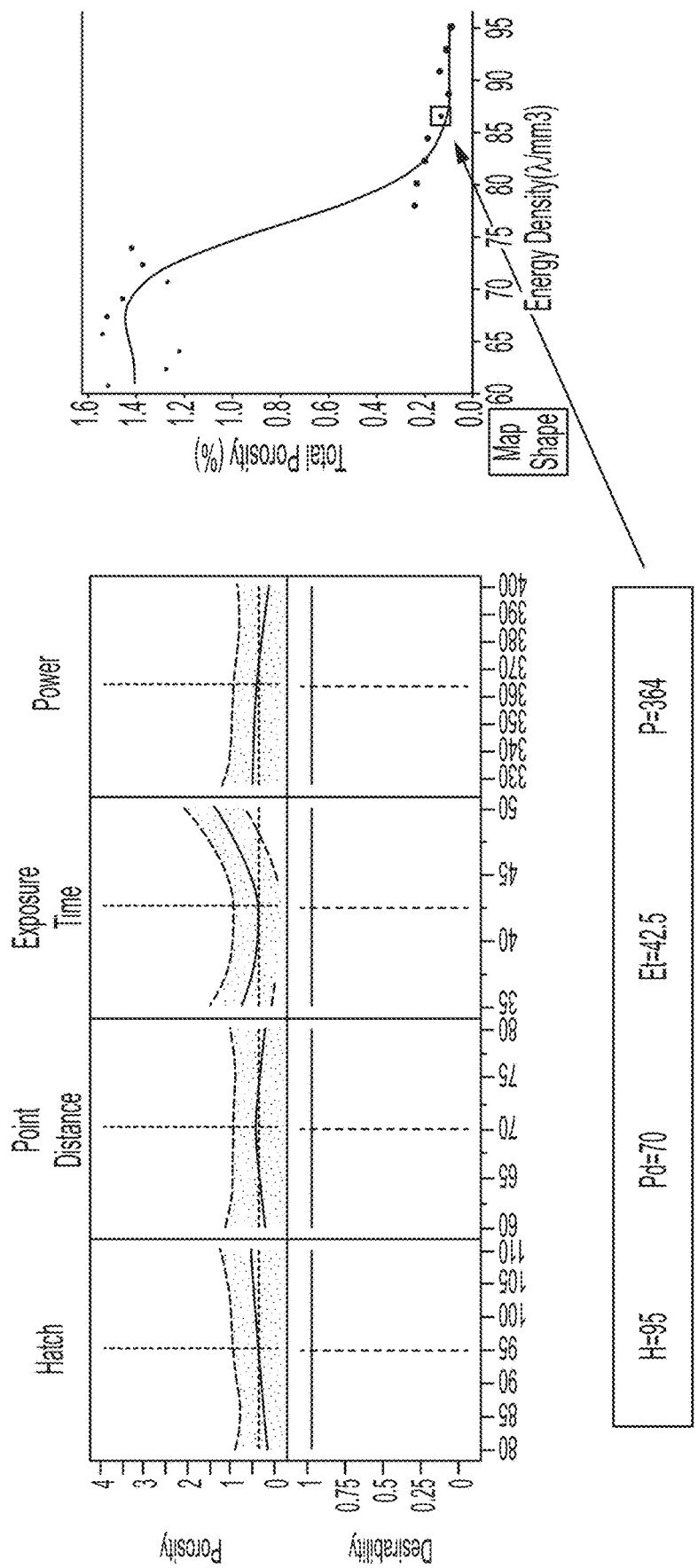
FIG. 3 graphically illustrates porosity as a function of desirability in a statistical analysis of various additive manufacturing process parameters and desirability parameter validation graphically illustrating porosity as a function of energy density in accordance with the present disclosure.

FIG. 3 graphically illustrates an exemplary design of experiments (DOE) using JMP statistical software including adjusted desirability plots for minimal porosity for different parameters used to provide a certain energy density. The different laser processing parameters included hatch spacing, point distance, exposure time, and power parameters in an L-PBF AM process. The interaction of these parameters is rather complex and the optimized parameter set based on the desirability analysis of the relatively large orthogonal parameter space provided by the DOE and its effect on total porosity as a function of energy density using these parameters was independently confirmed as graphically shown. Total porosity as a percentage of total volume was measured using high throughput XRCT.

Figure 4:
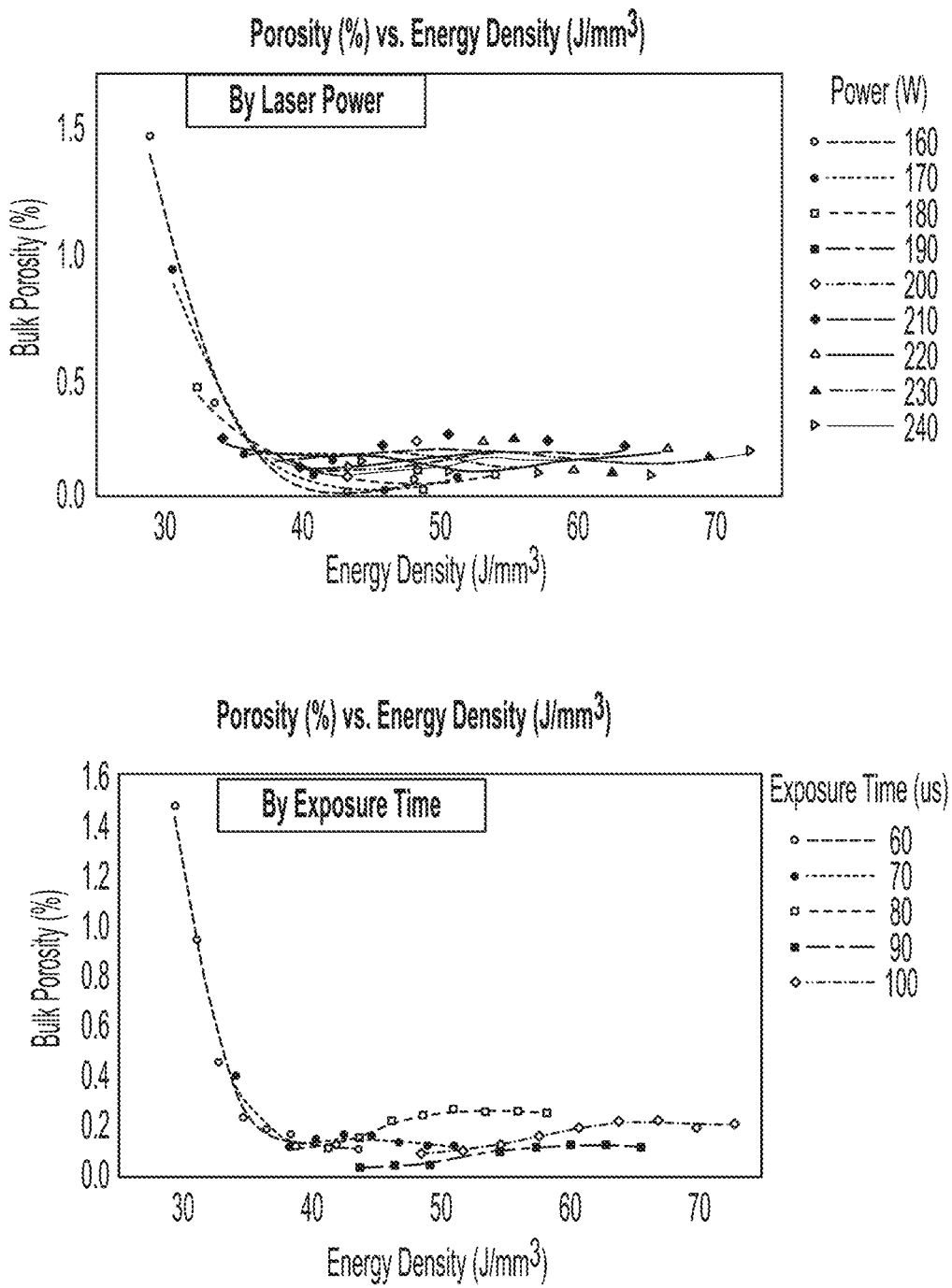
FIG. 4 graphically illustrates porosity as a function of energy density by laser power and by exposure time for samples made with a laser powder bed fusion additive manufacturing process in accordance with the present disclosure.

FIG. 4 illustrates a sample output of a DOE illustrating process parameter relationships on total porosity as a measured physical output. The graph on the left graphically illustrates porosity as a function of energy density by laser power and the graph on right illustrates porosity as a function of energy density by exposure time. The relationship and trends observed on porosity by laser power and by exposure time can be readily determined and further understood to provide an optimal parameter set that takes into account independent parameters as well as confounded parameters the sensitivities of each.

Figure 5:
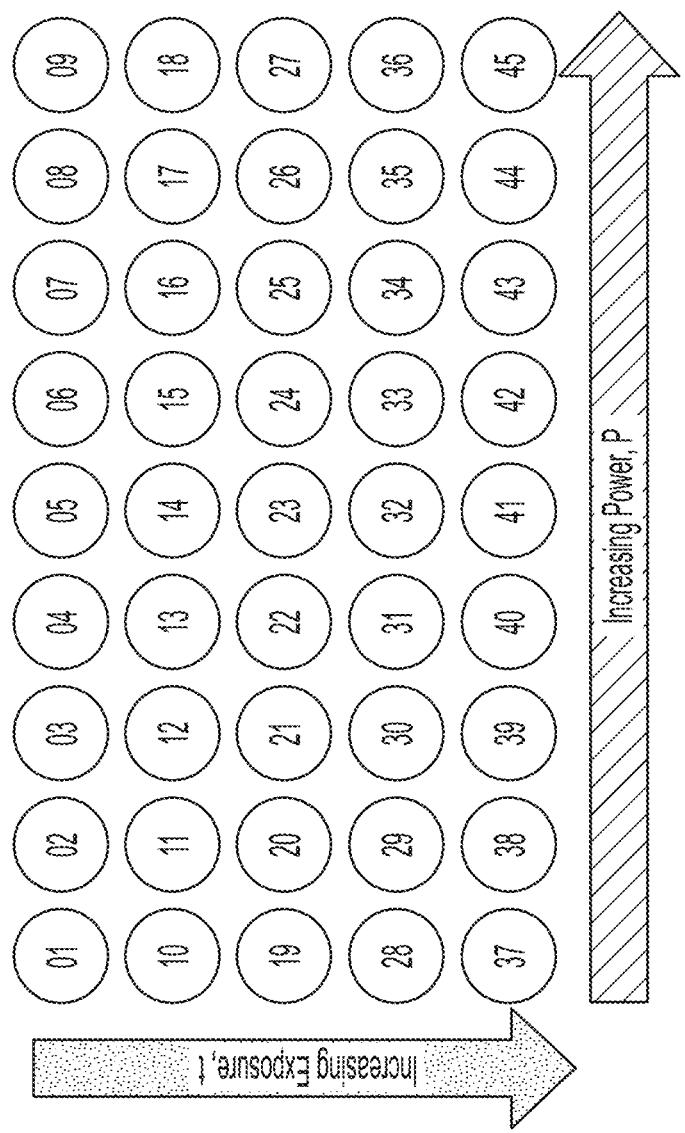
FIG. 5 schematically illustrates a design of experiment sample set based on exposure time and laser power for a laser powder bed fusion additive manufacturing process in accordance with the present disclosure.

Referring now to FIGS. 5-8, a rapid development process for optimizing a parameter space associated with additive manufacturing was generated for a steel alloy composition. FIG. 5 illustrates a DOE based on hatch spacing, point distance, velocity and power as parameters using statistical software that can provide an orthogonal output using a Latin-hypercube sampling method or the like. Exemplary commercially available statistical software that can be configured to provide various sampling methods to produce an orthogonal output includes JMP software. The DOE was configured to provide a linear progression in power and exposure times for total porosity using an estimate of the optimal settings. Other laser input parameters that can be included in a DOE include but are not limited to power, velocity, hatch, point distance, exposure time and machine parameters such as recoating time, layer thickness, or the like. As shown, each of the various rows of the reduced volume build samples were fabricated with constant exposure times and incremental increases in laser power whereas each of the various columns of the reduced build samples were fabricated with constant power with incremental increase in exposure times.

In this DOE, 45 reduced volume cylindrical samples were built to better understand and determine the ideal parameter space, e.g., hatch spacing, point distance, laser power, velocity, layer thickness, and the like, to provide an optimal parameter space that provides the most ideal melt pool solidification for the given steel alloy feedstock chemistry. The particular steel alloy is not intended to be limited and is intended to be exemplary of the process.

Figure 6:
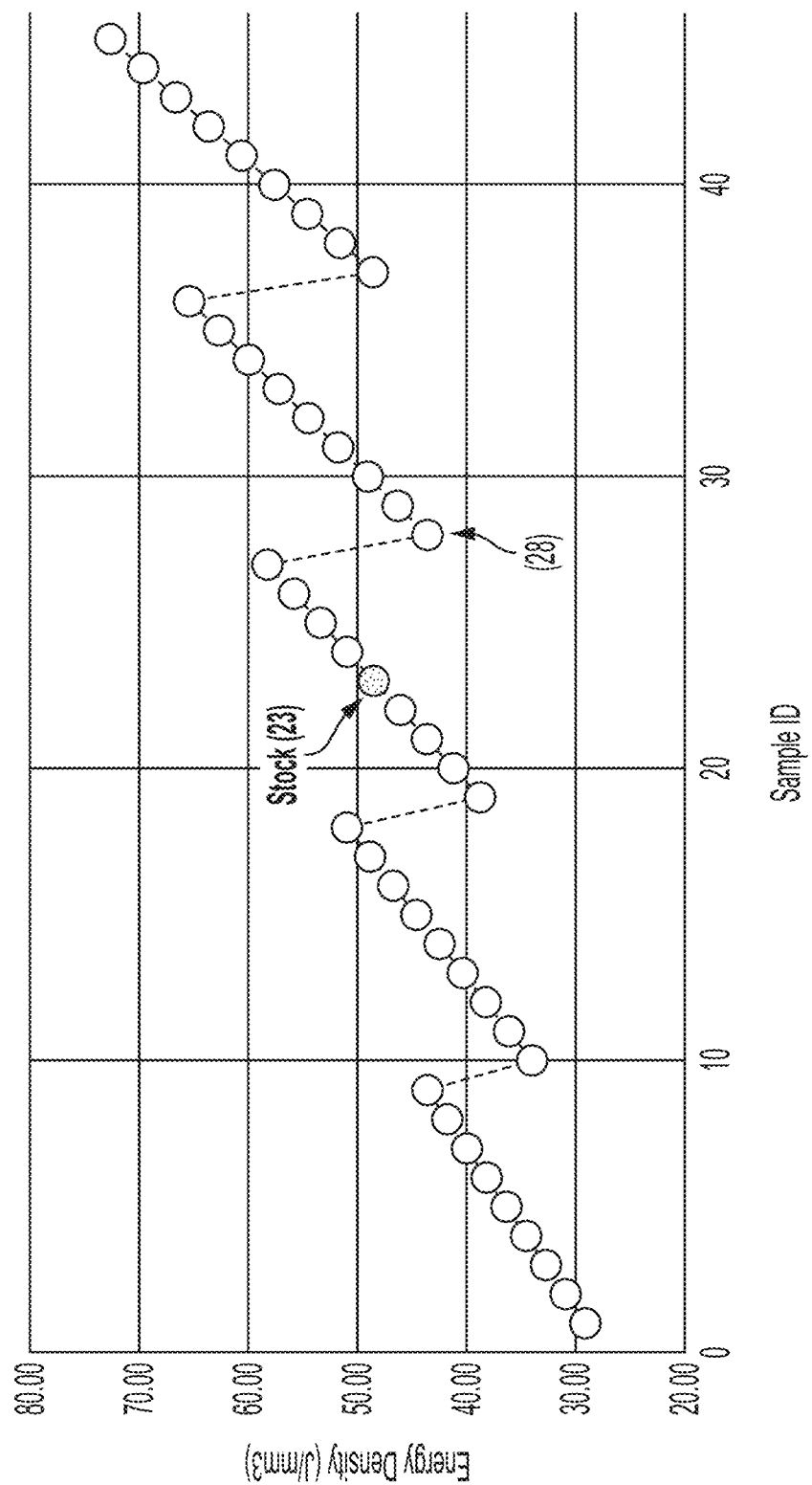
FIG. 6 graphically illustrates energy density for the design of experiment sample set of FIG. 5 in accordance with the present disclosure.

FIG. 6 graphically illustrates the resulting energy density for each of the samples. Sample ID 01 was fabricated with a laser power and exposure time that provided the lowest energy density; sample ID 45 was fabricated with a laser power and exposure time that provided the greatest energy density; sample ID 23 was fabricated with a laser power and exposure time in accordance with the manufacturers recommended processing parameters; and sample ID 28 was fabricated with a laser power and exposure time that provided the maximum density. High throughput XRCT was utilized to determine percent porosity associated with a specific parameter set. It should also be noted that ultimate tensile hardness and/or any other mechanical property including, but not limited to, compression, fatigue and/or the like can be examined as a physical output in a similar manner as may desired. Likewise, various microscopy techniques can be used including, but not limited to, scanning electron microscopy, energy dispersive microscopy, x-ray diffraction microscopy, and like high throughput non-beam-line techniques.

Figure 7:
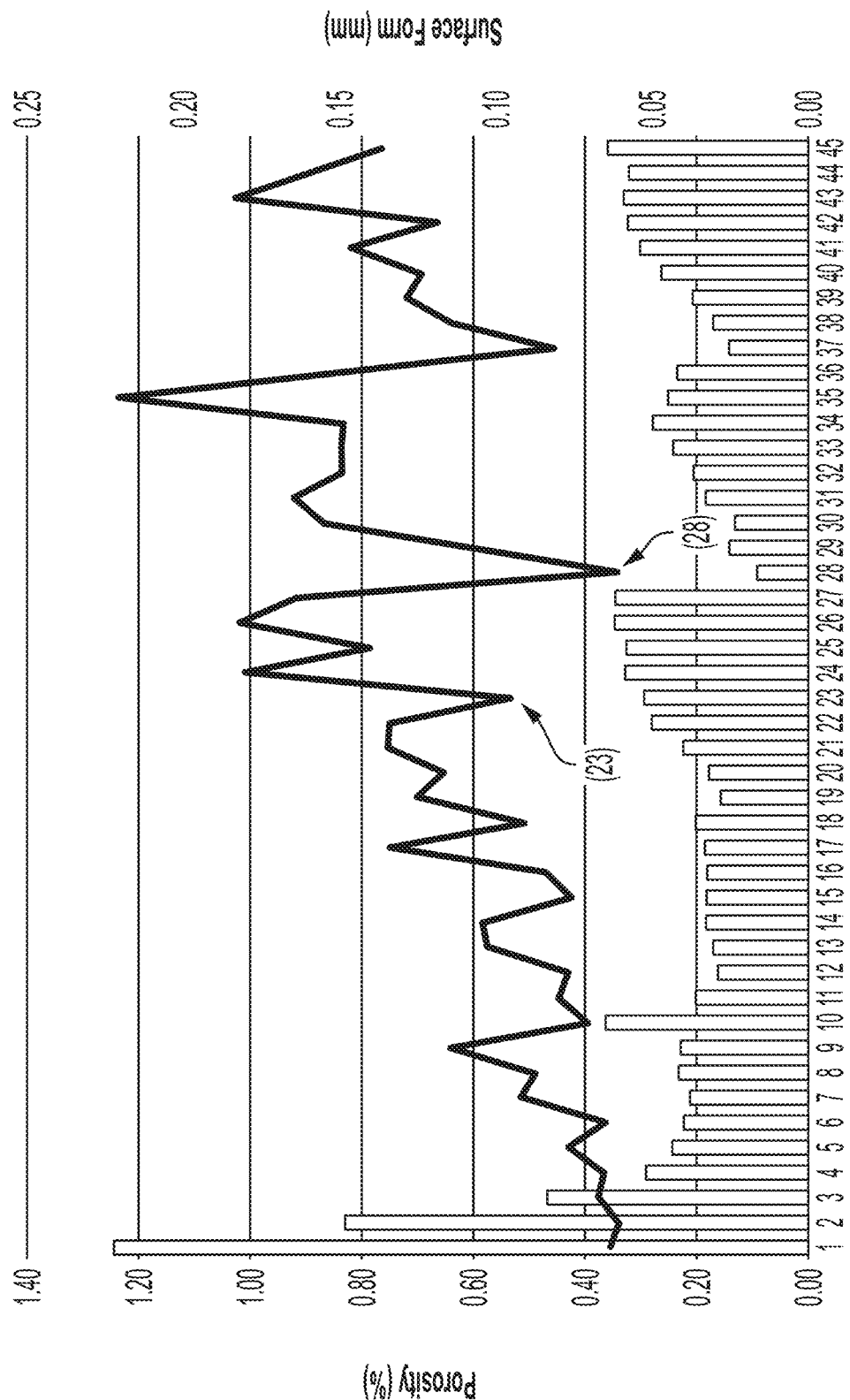
FIG. 7 graphically illustrates total porosity and deviation from sample form for the design of experiment sample set of FIG. 5 in accordance with the present disclosure FIG. 8 pictorially illustrates sectional views and 3D renderings of the porosity through a cylindrical volume for selected samples in the design of experiment sample set of FIG. 5 in accordance with the present disclosure.

FIG. 7 graphically illustrates the total porosity as a percentage of volume (bar graph) and sample form (line graph) for each of the samples in the sample set as measured using high throughput XRCT. The term "sample form" generally refers to the dimensional deviation from a "perfect" part or surface and is similar to surface roughness measurement. The XRCT process was configured to provide a cycle time for each sample of about 1 to 2 minutes with a voxel resolution of about 10 to 20 microns. In XRCT, an x-ray is transmitted through a sample and measured on a target. The sample is rotated and frames are taken at predetermined rotation intervals. This allows extraction of three-dimensional (3-D) defects in the sample based on stereographic projections. The intensity of the beam and rotation interval can be optimized to have a high signal to noise ratio. Trades in sample size and XRCT configurations are made to maximize detail while minimizing scan time.

As noted above, sample identification number 23 was the stock processing recipe recommended by the manufacturer, which provided a total porosity of about 0.295% and a sample form of about 0.9 mm whereas sample identification number 28 represented the optimal process and a marked improvement relative to the other samples, which provided the lowest total porosity of about 0.095% and a sample form of about 0.7 mm. For additional comparison, the samples built with the least energy density, sample identification number 01, had a total porosity of about 1.247% and a sample form of about 0.07 mm whereas the sample built with the greatest energy density, sample identification number 45, had a total porosity of about 0.360% and a surface form of about 0.14 mm.

Figure 8:
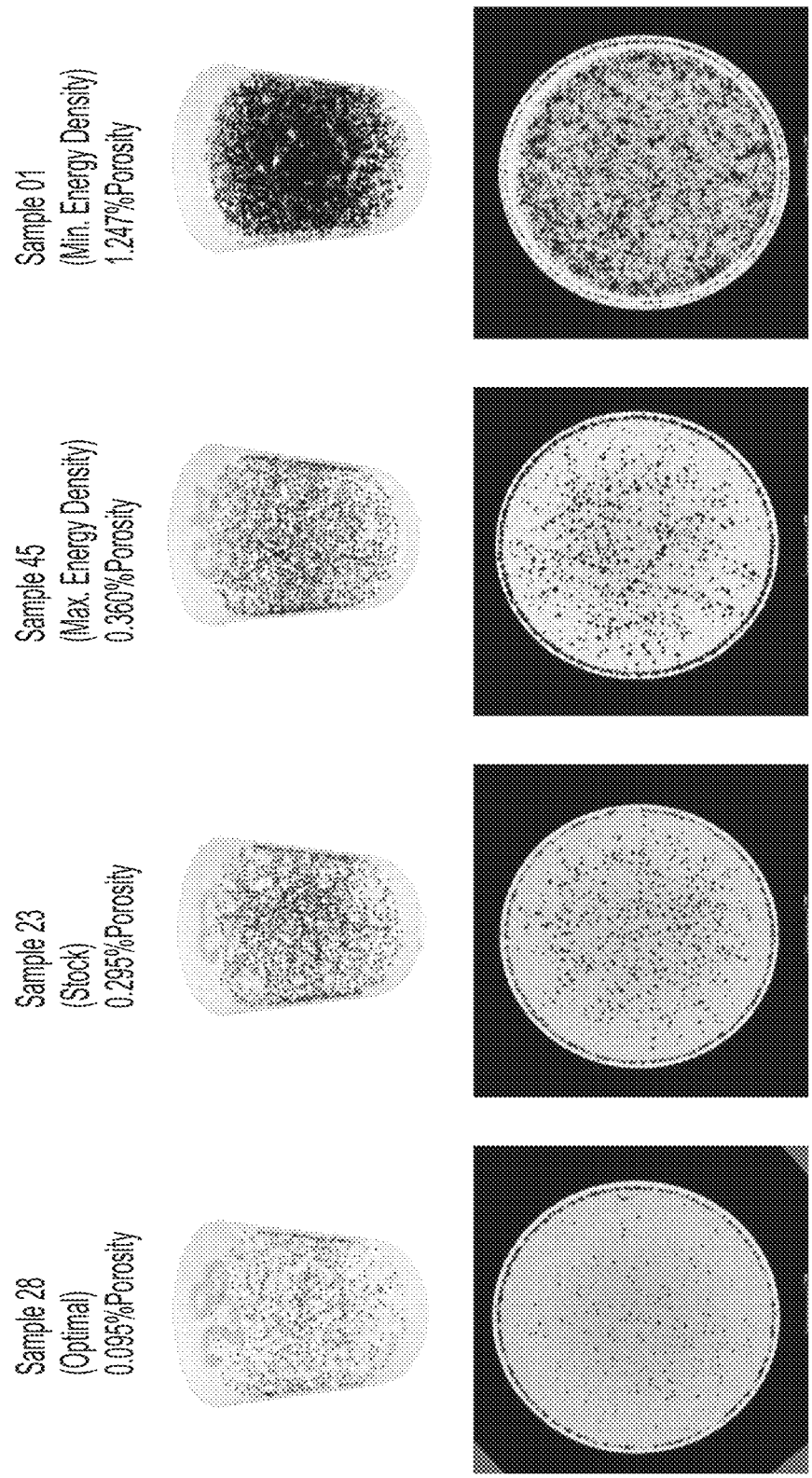

FIG. 8 pictorially illustrates a sectional view of the porosity and a 3D rendering through the cylindrical volume of sample identification numbers 01 (minimal energy density), 23 (stock), 28 (optimal), and 45 (maximum energy density) using high throughput XRCT. Lack of fusion porosity defects were evident in sample identification number 01 and keyhole defects were evident in sample identification numbers 23, 28 and 45.

Turning now to FIGS. 9-12, the process in accordance with the present disclosure was applied to an aluminum alloy. The aluminum alloy was a 5000 series aluminum alloy although the selection of a particular aluminum alloy is intended to be non-limiting and exemplary of the process.

Figure 9:
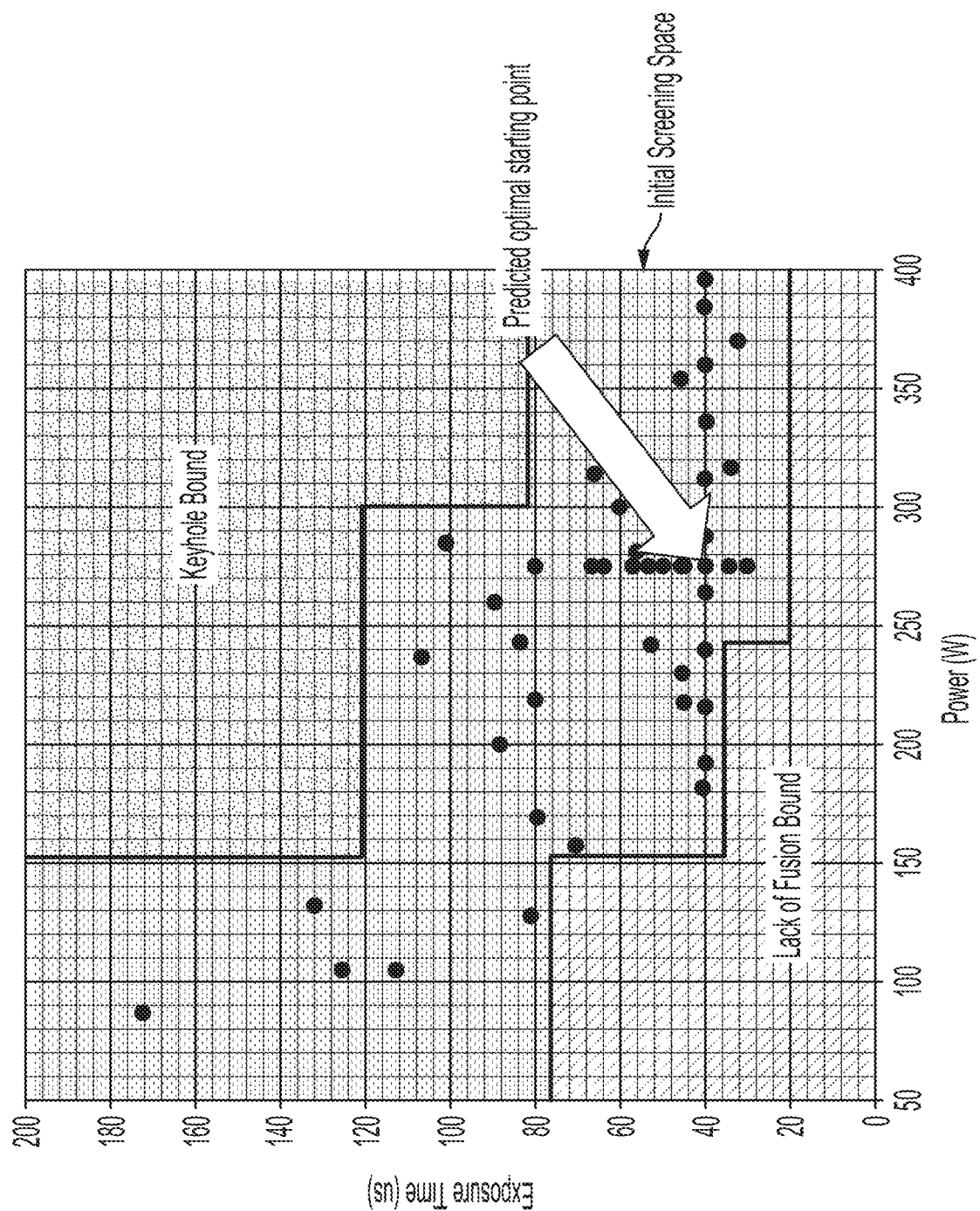
FIG. 9 graphically illustrates exposure time as a function of power for an additive manufacturing model depicting a predicted processing space including a modeled optimal initial setpoint in accordance with the present disclosure.

FIG. 9 graphically illustrates an optimal processing space as a function of exposure time and power based on a predicted optimal starting point obtained by computational modeling. Lack of fusion defects were generally predicted at the lower exposure times whereas keyhole bound defects were generally predicted with the higher power settings.

Figure 10:
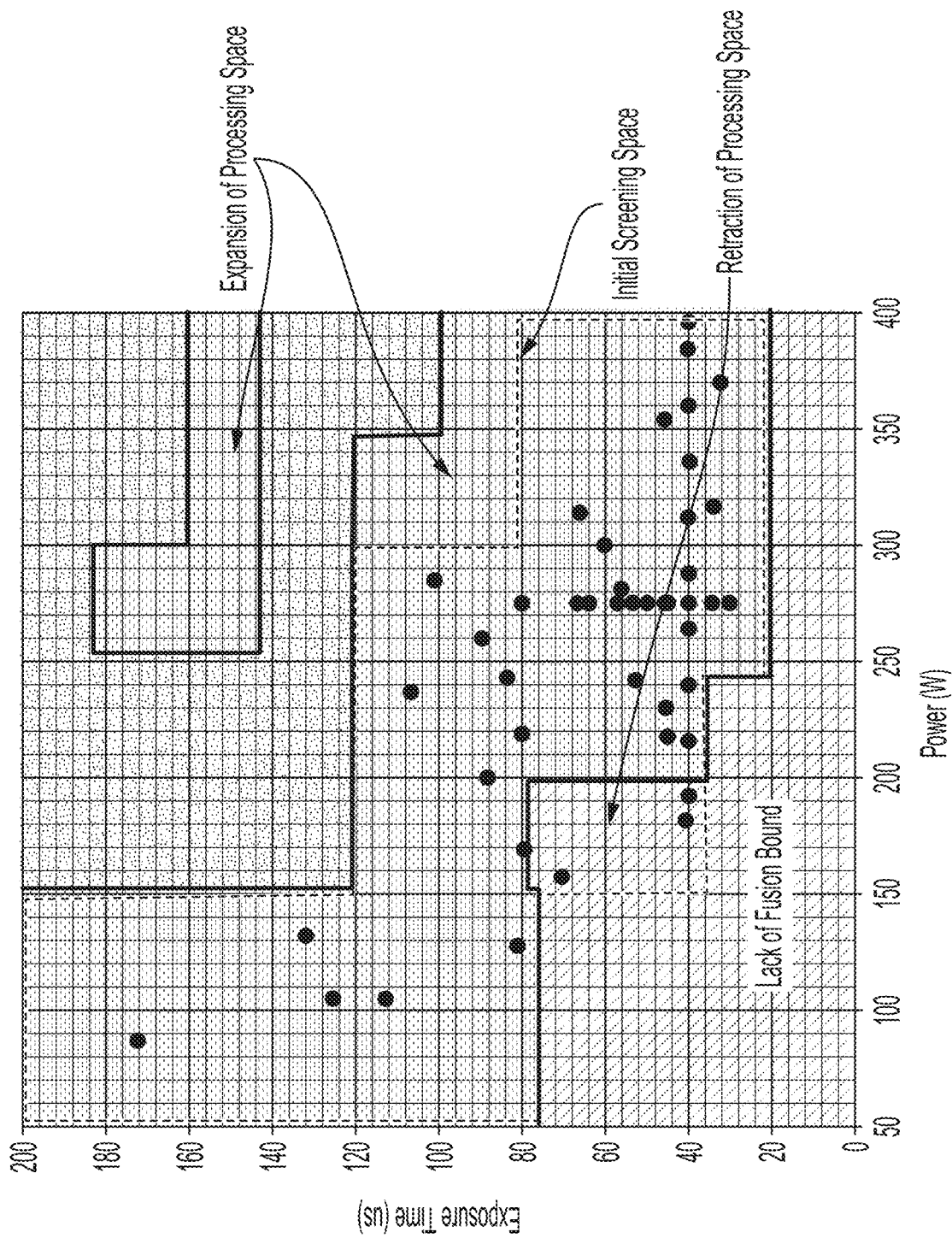
FIG. 10 graphically illustrates exposure time as a function of power for an additive manufacturing model subsequent to obtaining secondary information from a build cycle based on the modeled optimal initial setpoint of FIG. 9 in accordance with the present disclosure.

FIG. 10 graphically illustrates an updated model simulation subsequent to the addition of secondary information, i.e., training data, from the first iteration of the DOE about the predicted optimal starting point, which as shown can change the optimal processing space such that in some areas there is expansion of the processing space and in other areas there is contraction. In this manner, the process can advantageously utilize machine learning to learn from the data and continually improve the accuracy of the processing space over time. Machine learning models, such as those based on neural networks or other regression techniques, can be trained and fine-tuned on data collected as additional parts of the processing space are explored by fabricating and characterizing new samples.

The DOE included 52 reduced volume cylindrical samples and tension bars for different parameter sets shown in Table 1 below to better understand and determine the ideal parameter space, e.g., hatch spacing, point distance, laser power, velocity, and the like, to provide an optimal parameter space that provides the most ideal melt pool solidification for the 5086 aluminum alloy feedstock chemistry. Layer thickness was constant. The powdered feedstock chemistry generally included chromium in an amount within a range of 0.05 to 0.25 weight percent (wt %), a maximum of 0.1 wt % of copper, a maximum of 0.5 wt % of iron, magnesium within a range of 3.5 to 4.5 wt %, manganese within a range of 0.2 to 0.7 wt %, a maximum of wt % of silicon, a maximum of 0.15 wt % of titanium, a maximum of 0.25 wt % zinc with the remainder aluminum.

The reduced volume cylinders of the modified 5086 aluminum alloy were fabricated using a Renishaw AM400 AM printer having a diameter of 6 millimeters (mm) and a height of 10 mm, which were conducive to XRCT imaging of the entire cylindrical volume. These were manufactured alongside reduced size tension bars with 2 mm gauge for rapid screening of tension strength, yield strength, and ductility. Layer thickness was 30 micrometers (μm).

Table 1 provides the laser parameters used in the DOE to generate a particular energy density and the resulting measured physical properties for each sample.

TABLE 1

| Specimen | Power (W) | Exp. Time (μsec) | Pt Dist. (mm) | Hatch (mm) | Layer Thickness (mm) | Energy Density | Scal Core Porosity | Scal Contour Porosity | Scal Roughness | Ultimate Tensile Strength (MPa) | Elongation | Yield Strength | Modulus |
|---|---|---|---|---|---|---|---|---|---|---|---|---|---|
| 1 | 275 | 40 | 80 | 0.080 | 30.0 | 57.3 | 0.61 | 0.06 | 22.35 | 465.8 | 0.11 | 427.4 | 66.4 |
| 2 | 300 | 60 | 80 | 0.080 | 30.0 | 93.8 | 0.08 | 0.16 | 27.46 | 454.5 | 0.10 | 428.0 | 66.9 |
| 3 | 275 | 30 | 60 | 0.080 | 30.0 | 57.3 | 0.18 | 0.04 | 20.58 | 467.9 | 0.12 | 427.7 | 67.1 |
| 4 | 275 | 50 | 100 | 0.080 | 30.0 | 57.3 | 0.28 | 0.08 | 21.32 | 466.2 | 0.09 | 431.8 | 70.0 |
| 5 | 275 | 34 | 60 | 0.080 | 30.0 | 65.5 | 0.14 | 0.10 | 20.92 | 466.2 | 0.09 | 436.5 | 66.1 |
| 6 | 275 | 46 | 80 | 0.080 | 30.0 | 65.5 | 0.30 | 0.10 | 20.73 | 471.2 | 0.10 | 435.5 | 70.2 |
| 7 | 275 | 57 | 100 | 0.080 | 30.0 | 65.5 | 0.21 | 0.10 | 21.39 | 469.3 | 0.11 | 435.1 | 69.2 |
| 8 | 275 | 40 | 60 | 0.080 | 30.0 | 76.4 | 0.06 | 0.20 | 22.07 | 458.0 | 0.10 | 428.4 | 69.0 |
| 9 | 275 | 53 | 80 | 0.080 | 30.0 | 76.4 | 0.08 | 0.14 | 22.16 | 463.7 | 0.09 | 434.7 | 70.7 |
| 10 | 275 | 67 | 100 | 0.080 | 30.0 | 76.4 | 0.07 | 0.15 | 22.50 | 470.4 | 0.11 | 440.4 | 69.0 |
| 11 | 275 | 45 | 60 | 0.080 | 30.0 | 85.9 | 0.07 | 0.19 | 21.92 | 461.8 | 0.11 | 431.2 | 68.6 |
| 12 | 275 | 64 | 80 | 0.080 | 30.0 | 91.7 | 0.08 | 0.21 | 23.43 | 462.3 | 0.10 | 431.5 | 67.5 |
| 13 | 275 | 80 | 100 | 0.080 | 30.0 | 91.7 | 0.07 | 0.20 | 24.09 | 457.5 | 0.12 | 426.4 | 70.5 |
| 14 | 275 | 40 | 80 | 0.060 | 30.0 | 76.4 | 0.43 | 0.08 | 22.49 | 469.6 | 0.10 | 437.0 | 65.1 |
| 15 | 275 | 40 | 80 | 0.070 | 30.0 | 65.5 | 0.40 | 0.05 | 21.85 | 473.5 | 0.12 | 436.8 | 68.3 |
| 16 | 275 | 40 | 80 | 0.075 | 30.0 | 61.1 | 0.40 | 0.03 | 21.54 | 473.3 | 0.11 | 434.7 | 68.1 |
| 17 | 275 | 40 | 80 | 0.085 | 30.0 | 53.9 | 0.48 | 0.04 | 20.16 | 474.7 | 0.10 | 435.7 | 72.0 |
| 18 | 275 | 40 | 80 | 0.090 | 30.0 | 50.9 | 0.57 | 0.05 | 21.32 | 468.5 | 0.10 | 431.0 | 67.9 |
| 19 | 275 | 40 | 80 | 0.100 | 30.0 | 45.8 | 0.76 | 0.08 | 20.63 | 462.5 | 0.08 | 424.5 | 64.4 |
| 20 | 192 | 40 | 80 | 0.080 | 30.0 | 40.0 | 6.89 | 2.18 | 20.77 | 408.6 | 0.02 | 384.1 | 58.8 |
| 21 | 216 | 40 | 80 | 0.080 | 30.0 | 45.0 | 4.11 | 0.99 | 21.49 | 443.5 | 0.05 | 409.5 | 66.8 |
| 22 | 240 | 40 | 80 | 0.080 | 30.0 | 50.0 | 1.76 | 0.27 | 19.86 | 459.5 | 0.09 | 419.3 | 67.5 |
| 23 | 264 | 40 | 80 | 0.080 | 30.0 | 55.0 | 0.64 | 0.07 | 20.98 | 466.8 | 0.08 | 432.6 | 70.9 |
| 24 | 288 | 40 | 80 | 0.080 | 30.0 | 60.0 | 0.24 | 0.09 | 21.16 | 469.0 | 0.09 | 437.3 | 67.4 |
| 25 | 312 | 40 | 80 | 0.080 | 30.0 | 65.0 | 0.12 | 0.24 | 21.46 | 462.8 | 0.09 | 433.5 | 70.4 |
| 26 | 336 | 40 | 80 | 0.080 | 30.0 | 70.0 | 0.14 | 0.56 | 22.58 | 454.7 | 0.07 | 434.0 | 65.5 |
| 27 | 360 | 40 | 80 | 0.080 | 30.0 | 75.0 | 0.33 | 1.02 | 22.31 | 440.4 | 0.06 | 419.6 | 65.0 |
| 28 | 384 | 40 | 80 | 0.080 | 30.0 | 80.0 | 0.72 | 1.44 | 23.66 | 434.5 | 0.06 | 414.8 | 65.3 |
| 29 | 396 | 40 | 80 | 0.080 | 30.0 | 82.5 | 0.72 | 1.33 | 24.44 | 424.8 | 0.05 | 409.1 | 63.6 |
| 30 | 370 | 32 | 67 | 0.100 | 30.0 | 59.6 | 0.24 | 0.54 | 22.45 | 464.8 | 0.08 | 434.5 | 70.0 |
| 31 | 317 | 34 | 60 | 0.100 | 30.0 | 60.0 | 0.16 | 0.38 | 20.89 | 463.7 | 0.08 | 433.9 | 69.8 |
| 32 | 354 | 46 | 90 | 0.100 | 30.0 | 60.0 | 0.14 | 0.41 | 21.08 | 465.4 | 0.07 | 430.4 | 70.4 |
| 33 | 169 | 80 | 75 | 0.100 | 30.0 | 60.0 | 0.57 | 0.10 | 19.85 | 464.1 | 0.08 | 434.6 | 68.0 |
| 34 | 242 | 53 | 71 | 0.100 | 30.0 | 60.0 | 0.05 | 0.03 | 21.04 | 471.3 | 0.11 | 436.5 | 68.7 |
| 35 | 260 | 90 | 94 | 0.085 | 30.0 | 97.1 | 0.08 | 0.19 | 23.06 | 447.2 | 0.11 | 421.5 | 65.2 |
| 36 | 105 | 113 | 45 | 0.090 | 30.0 | 97.5 | 4.12 | 1.14 | 20.42 | 441.4 | 0.02 | 422.4 | 66.6 |
| 37 | 105 | 125 | 50 | 0.090 | 30.0 | 97.5 | 3.96 | 1.11 | 20.40 | 436.9 | 0.02 | 422.0 | 67.1 |
| 38 | 300 | 60 | 60 | 0.100 | 30.0 | 100.0 | 0.20 | 0.43 | 26.14 | 399.9 | 0.05 | 379.4 | 60.7 |
| 39 | 243 | 83 | 84 | 0.080 | 30.0 | 100.6 | 0.04 | 0.02 | 23.14 | 459.7 | 0.13 | 432.5 | 65.6 |
| 40 | 285 | 101 | 84 | 0.110 | 30.0 | 103.9 | 0.10 | 0.16 | 27.86 | 429.7 | 0.10 | 397.6 | 62.8 |
| 41 | 314 | 66 | 82 | 0.080 | 30.0 | 105.5 | 0.10 | 0.29 | 28.52 | 443.8 | 0.09 | 417.7 | 64.9 |
| 42 | 128 | 81 | 40 | 0.080 | 30.0 | 108.2 | 2.46 | 0.53 | 22.60 | 462.7 | 0.06 | 441.6 | 70.2 |
| 43 | 281 | 56 | 95 | 0.050 | 30.0 | 110.8 | 0.36 | 0.09 | 25.21 | 468.2 | 0.11 | 435.3 | 68.4 |
| 44 | 219 | 80 | 96 | 0.050 | 30.0 | 121.9 | 0.55 | 0.06 | 25.43 | 473.5 | 0.13 | 447.0 | 70.8 |
| 45 | 132 | 132 | 40 | 0.050 | 30.0 | 290.4 | 1.35 | 0.17 | 24.91 | 453.7 | 0.12 | 444.2 | 72.7 |
| 46 | 200 | 88 | 40 | 0.050 | 30.0 | 294.3 | 0.41 | 0.02 | 30.47 | 472.5 | 0.05 | 462.4 | 72.1 |
| 47 | 87 | 172 | 40 | 0.040 | 30.0 | 313.6 | 5.44 | 1.36 | 20.85 | 399.0 | 0.01 | 391.9 | 63.2 |
| 48 | 237 | 107 | 60 | 0.040 | 30.0 | 351.4 | 0.11 | 0.17 | 33.95 | 441.1 | 0.11 | 425.6 | 68.4 |
| 49 | 157 | 71 | 95 | 0.065 | 30.0 | 60.3 | 3.35 | 0.70 | 20.85 | 443.3 | 0.02 | 418.8 | 65.6 |
| 50 | 182 | 41 | 63 | 0.065 | 30.0 | 60.3 | 1.13 | 0.15 | 21.05 | 463.6 | 0.09 | 429.2 | 67.4 |
| 51 | 218 | 45 | 84 | 0.065 | 30.0 | 60.3 | 2.18 | 0.31 | 20.87 | 440.8 | 0.03 | 412.0 | 64.6 |
| 52 | 230 | 45 | 89 | 0.065 | 30.0 | 60.3 | 1.92 | 0.27 | 20.44 | 450.4 | 0.07 | 414.7 | 65.3 |

Ultimate Tensile Strength (mPa);
Yield Strength (Mpa);
Modulus (Gpa);
Elongation (mm/mm)

Figures 11, 12:
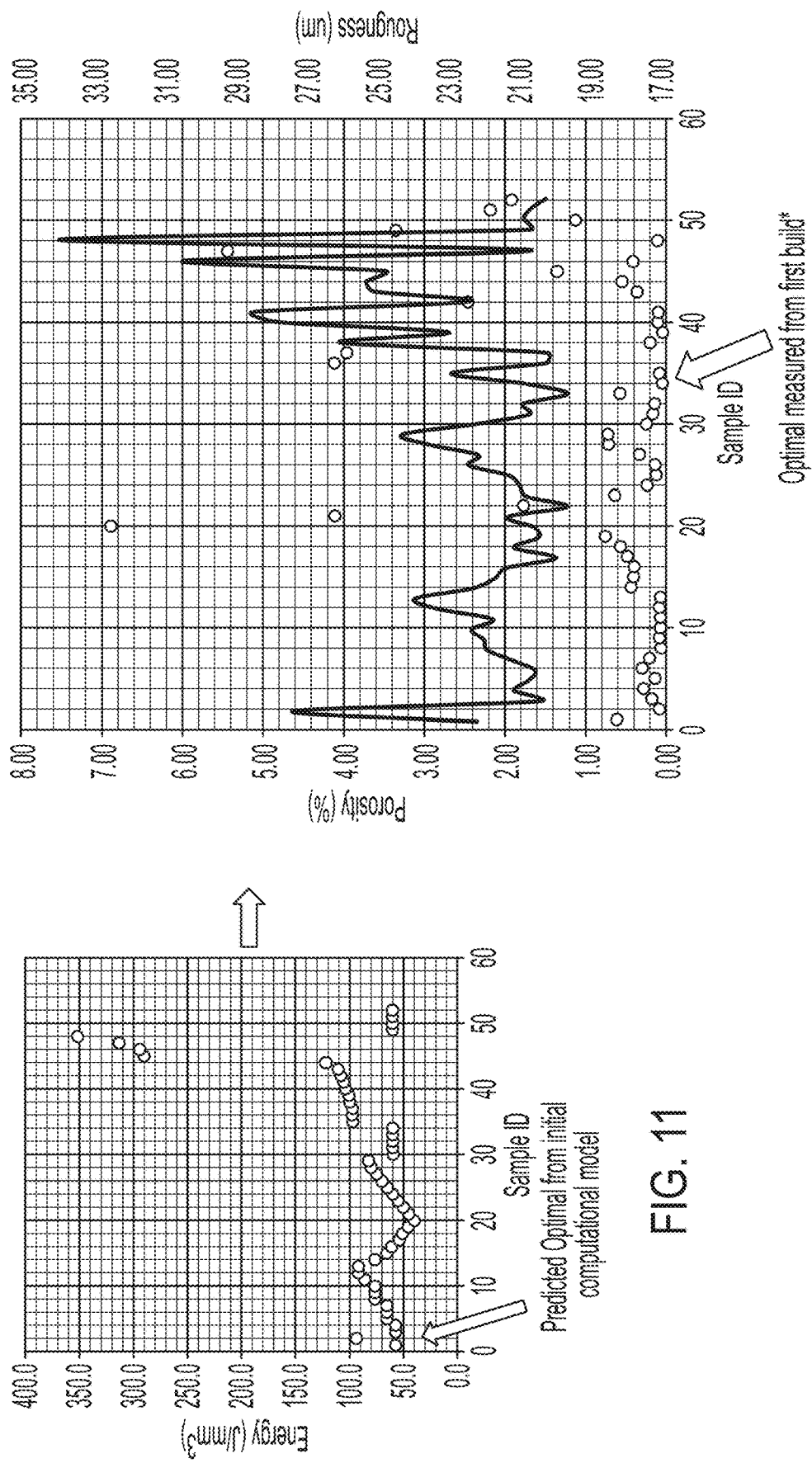
FIG. 11 graphically illustrates build samples from a multifactorial design for energy density based on a modeled optimal initial setpoint in accordance with the present disclosure.
FIG. 12 graphically illustrates total porosity and surface roughness for the build samples in accordance with the present disclosure.

FIG. 11 graphically illustrates energy density for the different aluminum alloy samples. The model simulation predicted the optimal predicted sample to be associated with specimen 1, i.e., sample 1. However, as shown in FIG. 12, the DOE about the parameter space associated with sample 1 indicated that sample 34 yielded the optimal results in terms of porosity and surface roughness, Sample 1 exhibited a total porosity of 0.62% by volume (vol %) and a surface roughness of 22.35 μm whereas Sample 34 exhibited a markedly lower total porosity of 0.05 vol % and a surface roughness of 21.04 It is important to note that results for the porosity and surface roughness properties were after a single build. It can be expected that machine learning can be used, if needed, to further optimize and improve upon the porosity and surface roughness properties after additional secondary information is obtained with an additional DOE and sample build about the parameter space of Sample 34. In this case, machine learning models, such as neural networks or other regression-based methods, can be trained to approximate the relationship between build input parameters (such as power, hatch, speed) and material properties (such as porosity and surface roughness). Moreover, the processing space about a particular optimum can be determined to provide an end user with information concerning the stability of the process associated with a particular feedstock chemistry and additive manufacturing device.

Figure 13:
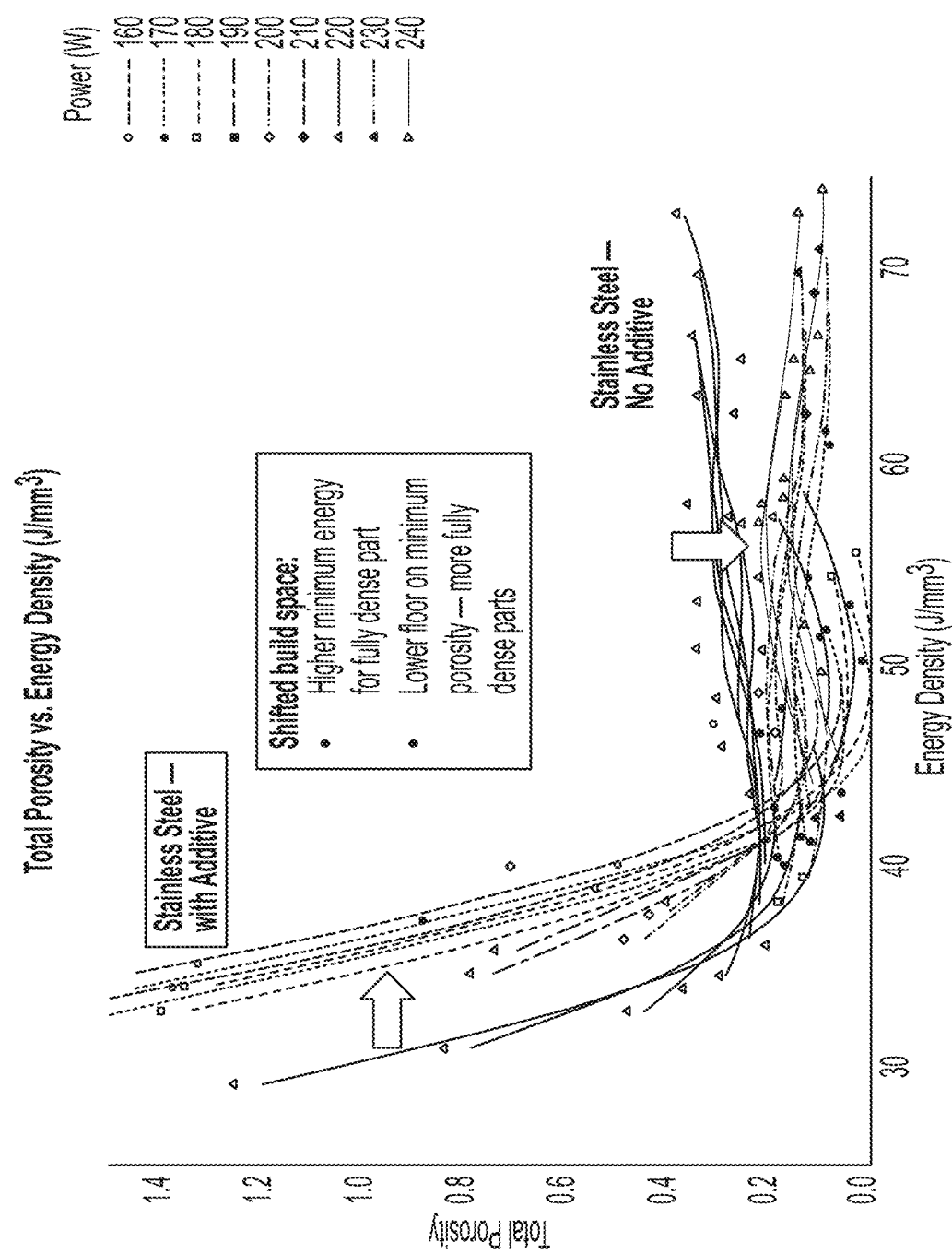
FIG. 13 graphically illustrates total porosity as a function of energy density for a type 316L steel feedstock chemistry with and without a ceramic additive manufactured with a laser powder bed fusion additive manufacturing process in accordance with the present disclosure.

Turning now to FIG. 13, there is graphically shown the effect of feedstock chemistry on total porosity as a function of energy density for a metal alloy composition with and without 5% by weight a dopant material using a DOE parameter space defined by CFD simulation. Total porosity was determined using high throughput XRCT. As shown, the addition of the dopant material to the metal alloy powder feed composition shifted the build space resulting in a higher minimum energy compared to the behavior of additive manufactured metal alloy composition without the dopant material. However, as shown, a lower floor on minimum porosity was also advantageously observed for the metal alloy composition with the dopant material compared to the behavior of metal alloy composition without the dopant material. From this design of experiment data, a robust processing parameter space based on parameter relationships and trends can be selected to provide minimal total porosity as well as minimal energy density requirements that provides the desired amount of total porosity.

Figure 14:
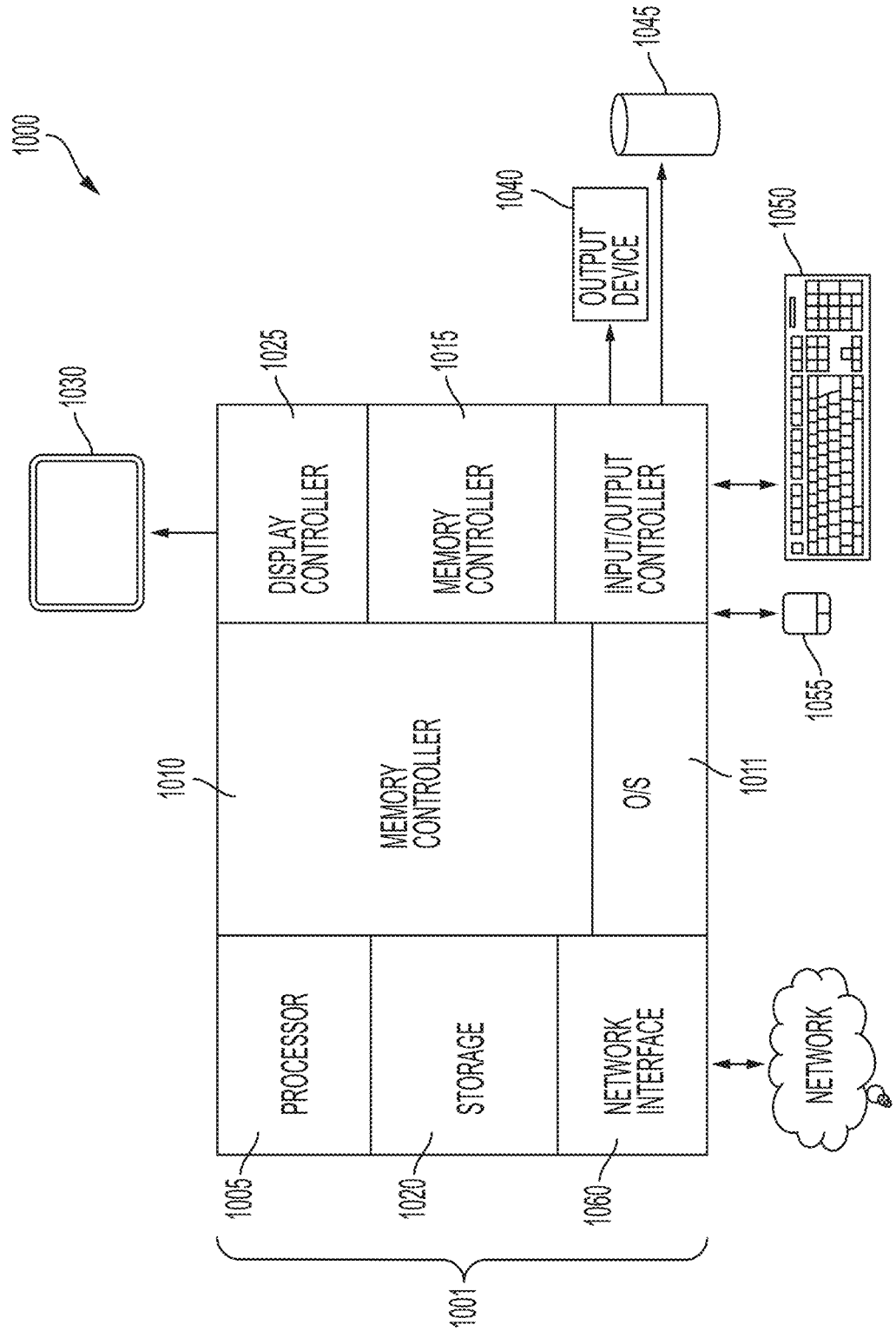
FIG. 14 illustrates an exemplary computer system for the rapid development additive manufacturing method of in accordance with one or more embodiments of the present disclosure.

FIG. 14 illustrates an exemplary computer system 1000 for the rapid development additive manufacturing method of in accordance with one or more embodiments of the present disclosure. The methods described herein can be implemented in hardware, software (e.g., firmware), or a combination thereof. In one or more exemplary embodiments of the present disclosure, the methods including the computational fluid dynamic simulation, design of experiments, and the AM apparatus and subsequent analysis of one or more physical outputs described herein are implemented in hardware as part of the microprocessor of a special or general-purpose digital computer, such as a personal computer, workstation, minicomputer, or mainframe computer. The system 1000 therefore may include general-purpose computer or mainframe 1001 capable of running multiple instances of an O/S simultaneously.

In one or more exemplary embodiments of the present disclosure, in terms of hardware architecture, the computer 1001 includes one or more processors 1005, memory 1010 coupled to a memory controller 1015, and one or more input and/or output (I/O) devices 1040, 1045 (or peripherals) that are communicatively coupled via a local input/output controller 1035. The input/output controller 1035 can be, for example but not limited to, one or more buses or other wired or wireless connections, as is known in the art. The input/output controller 1035 may have additional elements, which are omitted for simplicity, such as controllers, buffers (caches), drivers, repeaters, and receivers, to enable communications. Further, the local interface may include address, control, and/or data connections to enable appropriate communications among the aforementioned components. The input/output controller 1035 may include a plurality of sub-channels configured to access the output devices 1040 and 1045. The sub-channels may include fiber-optic communications ports.

The processor 1005 is a hardware device for executing software including CFD, DOE, ANI processing software and/or physical output analytical software, particularly that stored in storage 1020, such as cache storage, or memory 1010. The processor 1005 can be any custom made or commercially available processor, a central processing unit (CPU), an auxiliary processor among several processors associated with the computer 1001, a semiconductor based microprocessor (in the form of a microchip or chip set), a macroprocessor, or generally any device for executing instructions.

The memory 1010 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 1010 may incorporate electronic, magnetic, optical, and/or other types of storage media. Note that the memory 1010 can have a distributed architecture, where various components are situated remote from one another, but can be accessed by the processor 1005.

The instructions in memory 1010 may include one or more separate programs, each of which comprises an ordered listing of executable instructions for implementing logical functions. In the example of FIG. 14, the instructions in the memory 1010 provides a suitable operating system (OS) 1011. The operating system 1011 essentially controls the execution of other computer programs and provides scheduling, input-output control, file and data management, memory management, and communication control and related services. In one or more embodiments, the instructions, e.g., code, can be stored on a non-transitory computer readable medium, wherein the term "non-transitory" generally refers to computer-readable media that stores data for short periods or in the presence of power such as a memory device or Random Access Memory (RAM).

In accordance with one or more embodiments of the present invention, the memory 1010 may include multiple logical partitions (LPARs) each running an instance of an operating system. The LPARs may be managed by a hypervisor, which may be a program stored in memory 1010 and executed by the processor 1005.

In one or more exemplary embodiments of the present disclosure, a conventional keyboard 1050 and mouse 1055 can be coupled to the input/output controller 1035. Other output devices such as the I/O devices 1040, 1045 may include input devices, for example but not limited to a printer, a scanner, microphone, and the like. Finally, the I/O devices 1040, 1045 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 1000 can further include a display controller 1025 coupled to a display 1030.

In one or more exemplary embodiments of the present disclosure, the system 1000 can further include a network interface 1060 for coupling to a network 1065. The network 1065 can be an IP-based network for communication between the computer 1001 and any external server, client and the like via a broadband connection. The network 1065 transmits and receives data between the computer 1001 and external systems, e.g., an AM printer. In an exemplary embodiment, network 1065 can be a managed IP network administered by a service provider. The network 1065 may be implemented in a wireless fashion, e.g., using wireless protocols and technologies, such as WiFi, WiMax, etc. The network 1065 can also be a packet-switched network such as a local area network, wide area network, metropolitan area network, Internet network, or other similar type of network environment. The network 1065 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 1001 is a PC, workstation, intelligent device or the like, the instructions in the memory ZZ10 may further include a basic input output system (BIOS) (omitted for simplicity). The BIOS is a set of essential software routines that initialize and test hardware at startup, start the OS 1011, and support the transfer of data among the hardware devices. The BIOS is stored in ROM so that the BIOS can be executed when the computer 1001 is activated.

When the computer 1001 is in operation, the processor 1005 is configured to execute instructions stored within the memory 1010, to communicate data to and from the memory 1010, and to generally control operations of the computer 1001 pursuant to the instructions.

The computer-readable medium can be a manufactured product, such as hard drive in a computer system or an optical disc sold through retail channels, or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PD), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM (Erasable Programmable Read-Only Memory), EEPROM (Electrically Erasable Programmable Read-Only Memory), and flash memory devices; magnetic disks, internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The computing system can include clients and servers. A client and server are generally remote from each other and typically interact through a communication network. The relationship of client and server arises by virtue of computer programs running on the respective computers and having a client-server relationship to each other. Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network.

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software, products.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer implemented powder bed fusion rapid material development process for additive manufactured materials, the computer implemented process comprising:
    modeling melt pool solidification of powder bed fusion additive manufactured materials to produce a simulated parameter set;
    designing a multi-factorial parameter space encompassing the simulated parameter set;
    building multiple additive manufactured samples for each parameter set within the multi-factorial parameter space, wherein each parameter set comprises independent parameters comprising one or more of a layer thickness, hatch spacing, exposure time, scan velocity, power or combinations thereof, and wherein the additive manufactured samples are at a reduced volume relative to an intended build article;
    mechanically characterizing one or more physical outputs for each of the additive manufactured samples built according to each parameter set; and
    correlating defect morphology associated with the one or more physical outputs to one or more independent parameters within the multi-factorial parameter space used in building the multiple additive manufactured samples to provide an optimal parameter set.

2. The computer implemented powder bed fusion rapid material development process for additive manufactured materials of claim 1, wherein mechanically characterizing comprises measure total porosity within a volume of additive manufactured sample by subjecting each of the additive manufactured samples to x-ray computed tomography with cycle times of about 1 to about 2 minutes.

3. The computer implemented powder bed fusion rapid material development process for additive manufactured materials of claim 1, wherein the powder bed fusion additive manufacturing process is a laser powder bed fusion manufacturing process or a directed energy deposition process.

4. The computer implemented powder bed fusion rapid material development process for additive manufactured materials of claim 1, wherein the powder bed fusion additive manufacturing process is an electron beam powder bed fusion manufacturing process.

5. The computer implemented powder bed fusion rapid material development process for additive manufactured materials of claim 1, wherein the defect morphology comprises total porosity as a function of energy density.

6. The computer implemented powder bed fusion rapid material development process for additive manufactured materials of claim 1, wherein modeling melt pool solidification comprises a computational fluid dynamics analysis.

7. The computer implemented powder bed fusion rapid material development process for additive manufactured materials of claim 1, wherein mechanically characterizing the one or more physical outputs comprises optical and X-ray microscopy, Archimedes method, microhardness, tensile strength, or combinations thereof.

8. The computer implemented powder bed fusion rapid material development process for additive manufactured materials of claim 1, wherein building the multiple additive manufactured samples comprises building reduced volume samples that are a fraction of an intended build article.

9. A computer implemented powder bed fusion rapid material development process for additive manufactured materials, the computer implemented process comprising:
    utilizing a computer fluid dynamic simulation to establish a baseline simulated parameter space for a given material that predicts a desired melt pool shape and solidification for the given material;
    selecting a simulated parameter set from within the parameter space;
    defining an orthogonal parameter space with a design of experiments encompassing the simulated parameter set;
    preparing reduced volume samples in accordance with actual parameter sets within the orthogonal parameter space;
    mechanically characterizing each of the reduced volume samples; and
    determining an optimal build parameter set from the actual parameter sets based on the mechanical characterization of the reduced volume samples.

10. The computer implemented powder bed fusion rapid material development process for additive manufactured materials of claim 9, wherein the computer fluid dynamic simulation provides simulations of the melt pool shape and solidification for the given material.

11. The computer implemented powder bed fusion rapid material development process for additive manufactured materials of claim 9, wherein mechanically characterizing comprises characterizing porosity by surface roughness, tensile strength, hardness, density, dimensional accuracy, percent volume fraction, size and shape deviation, and/or type of defect.

12. The computer implemented powder bed fusion rapid material development process for additive manufactured materials of claim 9, wherein mechanically characterizing comprises exposing each of the reduced volume samples to x-ray computed tomography (XRCT) for the mechanical characterization.

13. The computer implemented powder bed fusion rapid material development process for additive manufactured materials of claim 12, wherein the XRCT is configured to provide a voxel resolution of about 1 to about 200 micrometers and a cycle time of about 1 to about 2 minutes for each of the reduced volume samples.

14. The computer implemented powder bed fusion rapid material development process for additive manufactured materials of claim 9, wherein the optimal parameter set comprises laser processing parameters comprising hatch spacing, point distance, laser power, velocity, and/or layer thickness.

15. The computer implemented powder bed fusion rapid material development process for additive manufactured materials of claim 9, wherein the reduced volume samples are fabricated with constant exposure times and incremental increases in laser power, and with constant power with incremental increases in exposure times.

16. The computer implemented powder bed fusion rapid material development process for additive manufactured materials of claim 9, wherein the given material is a feedstock for forming an aluminum alloy.

17. The computer implemented powder bed fusion rapid material development process for additive manufactured materials of claim 9, further comprising designing experiments for an orthogonal parameter space encompassing the optimal parameter set; preparing reduced volume samples in accordance with the orthogonal parameter space; mechanically characterizing each of the reduced volume samples; and determining a second optimal build parameter set based on the mechanical characterization of the reduced volume samples.

18. A computer implemented powder bed fusion rapid material development process for additive manufactured materials, the computer implemented process comprising:
preparing an experimental design about a selected parameter set;
additively manufacturing samples for each parameter set defined in the experimental design, wherein each parameter set comprises independent parameters comprising one or more of a layer thickness, hatch spacing, exposure time, scan velocity, power or combinations thereof, and wherein the additive manufactured samples are at a reduced volume relative to an intended build article;
mechanically characterizing one or more physical outputs for each of the additive manufactured samples built according to each parameter set; and
determining an optimal build parameter set on the mechanical characterization of the reduced volume samples.

19. The computer implemented powder bed fusion rapid material development process for additive manufactured materials of claim 18, wherein the parameter set is a manufacturer recommended parameter set for building an additively manufactured component.

20. The computer implemented powder bed fusion rapid material development process for additive manufactured materials of claim 18, wherein the parameter set is defined by computer fluid dynamic simulation.

* * * * *